(12) United States Patent
Pham-Schoenwetter et al.

(10) Patent No.: US 10,100,000 B2
(45) Date of Patent: Oct. 16, 2018

(54) METHOD FOR SYNTHESIZING 1,1-DIAMINO-2,2-DINITROETHYLENE (FOX-7) OR A SALT THEREOF

(71) Applicant: DIEHL DEFENCE GMBH & CO. KG, Ueberlingen (DE)

(72) Inventors: Oliver Pham-Schoenwetter, Lauf (DE); Bjoern Donner, Adelsdorf (DE); Arno Hahma, Henfenfeld (DE)

(73) Assignee: Diehl Defence GmbH & Co. KG, Ueberlingen (DE)

( * ) Notice: Subject to any disclaimer, the term of this patent is extended or adjusted under 35 U.S.C. 154(b) by 0 days.

(21) Appl. No.: 15/636,934

(22) Filed: Jun. 29, 2017

(65) Prior Publication Data
US 2018/0002270 A1 Jan. 4, 2018

(30) Foreign Application Priority Data

Jun. 29, 2016 (DE) .................. 10 2016 007 866

(51) Int. Cl.
*C07C 209/68* (2006.01)
*C07C 211/09* (2006.01)
*C07C 211/15* (2006.01)
*C07C 267/00* (2006.01)
*C07C 209/60* (2006.01)
*C07C 211/24* (2006.01)

(52) U.S. Cl.
CPC .......... *C07C 209/68* (2013.01); *C07C 209/60* (2013.01); *C07C 211/09* (2013.01); *C07C 211/15* (2013.01); *C07C 211/24* (2013.01); *C07C 267/00* (2013.01)

(58) Field of Classification Search
None
See application file for complete search history.

(56) References Cited

PUBLICATIONS

Nikolaj V. Latypov et al., "On the Synthesis of 1,1-Diamino-2,2-dinitroethene (FOX-7) by Nitration of 4,6-Dihydroxy-2-methylpyrimidine", Organic Process Research & Development, 2007, 11 (1), pp. 56-59.
Lochert, Ian J: "FOX-7—A New Insensitive Explosive", DSTO-TR-1238, DSTO Aeronautical and Maritime Research Laboratory, Australia, Nov. 2001.
Williams et al., "Carbodiimide Chemistry: Recent Advances", American Chemical Society, Chem. Rev. 1981, 81, pp. 589-636.
Nakano et al., Functionalized Carbodiimide Mediated Synthesis of 2,3-Disubstituted Quinazolin-4(3H)-ones via the Tandem Strategy of C-Nucleophilic Addition and Intramolecular NH-Substitution Cyclization, Synthesis, 2012, 44, pp. 3179-3184, http://www.organic-chemistry.org/abstracts/lit3/833.shtm.
Anniyappan, M., et al., "Synthesis, characterization and thermolysis of 1,1-diamino-2,2-dinitroethylene (FOX-7) and its salts". High Energy Materials Research Laboratory (HEMRL), Pune 411 021, India, Journal of Hazardous Materials B137, 2006, 812.

(Continued)

*Primary Examiner* — Clinton A Brooks
*Assistant Examiner* — Jennifer C Sawyer
(74) *Attorney, Agent, or Firm* — Laurence A. Greenberg; Werner H. Stemer; Ralph E. Locher

(57) ABSTRACT

In a method for synthesizing 1,1-diamino-2,2-dinitroethylene (FOX-7) or an N-substituted diamino derivative thereof or a salt of 1,1-diamino-2,2-dinitroethylene or of the N-substituted diamino derivative, a carbodiimide is reacted with a dinitromethane anion. The reaction of the carbodiimide with the dinitromethane anion takes place in a solution.

9 Claims, 2 Drawing Sheets

(56) References Cited

PUBLICATIONS

Holmgren, E., et al., "Energetic Materials", Reactions of Propellants, Explosives and Pyrotechnics, 34th International Annual Conference of ICT Jun. 24, Jun. 27, 2003, Karlsruhe, Federal Republic of Germany.

METHOD FOR SYNTHESIZING 1,1-DIAMINO-2,2-DINITROETHYLENE (FOX-7) OR A SALT THEREOF

CROSS-REFERENCE TO RELATED APPLICATION

This application claims the priority, under 35 U.S.C. § 119, of German application DE 10 2016 007 866.9, filed Jun. 29, 2016; the prior application is herewith incorporated by reference in its entirety.

BACKGROUND OF THE INVENTION

Field of the Invention

The invention relates to the synthesis of 1,1-diamino-2,2-dinitroethylene (FOX-7) or an N-substituted diamino derivative thereof or a salt of 1,1-diamino-2,2-dinitroethylene or of the derivative. Various methods are known for manufacturing FOX-7.

1. Nitration of a Nitrogen Heterocycle with Subsequent Hydrolysis to the End Product The synthesis is shown schematically in FIG. 1. The nitrogen heterocycle may be, for example, methylimidazole 3. Nitration thereof with $HNO_3/H_2SO_4$ leads to the formation of an intermediate 4 by nitration of the methyl group and an oxidation of the two carbon atoms of the imidazole ring not involved in bonding to the methyl group. The intermediate 4 decomposes partially at room temperature to a further intermediate 5, wherein FOX-7 1 is formed from both intermediates 4, 5 by hydrolysis in liquid ammonia. The problem in this synthesis is that the further intermediate 5 is very sensitive and readily explodes. Furthermore, the nitration reaction is comparatively inefficient. This results in a low overall yield of typically at most 13%.

2. Nitration of 2-methyl-2-methoxyimidazoledione (6)

The reaction is shown schematically in FIG. 2. The 2-methyl-2-methoxyimidazoledione 6 can be prepared by condensation of the compound 7 with acetamidine hydrochloride 8 in the presence of sodium methoxide in methanol. The nitration of 2-methyl-2-methoxyimidazoledione 6 typically enables an overall yield of up to 38%. A disadvantage of the method is that the resulting intermediate 9 is sensitive and readily explodes and that heat of reaction is formed during the reaction. Therefore, for safety reasons, the reaction must be carried out at high dilution. Comparatively large reaction vessels are thus required, whereby an industrial scale synthesis is uneconomic.

3. Nitration of 2-methyl-4,6-pyrimidinedione (10)

The method is shown schematically in FIG. 3. 2-Methyl-4,6-pyrimidinedione can be prepared from diethyl malonate 11 and acetamidine hydrochloride 8. The yield is around 80%. On hydrolysis of the nitrated intermediate 12, potassium dinitromethanate 13 is formed as by-product. Since potassium dinitromethanate is explosive and temperature-sensitive, it is necessary to carry out the nitration slowly and in a temperature-controlled manner. Conducting the reaction on an industrial scale is therefore comparatively expensive. After completion of the nitration, the potassium dinitromethanate 13 is removed by filtration.

Since FOX-7 is comparatively expensive up till now, it has found hardly any industrial application to date apart from in small amounts as booster charge in nuclear warheads, igniters and ignition enhancers. Due to its high performance and low sensitivity to shock, friction and thermal influences, FOX-7 would be attractive for many applications as a high-performance explosive, if it were more convenient to prepare. For example, it could be used in diverse applications as a less sensitive performance enhancer for spectral flares in decoy targets, as a performance enhancer in propellants and as a main charge. The object of the present invention is to provide an alternative method for the cost-effective preparation of FOX-7 or a derivative thereof.

SUMMARY OF THE INVENTION

A method for synthesizing 1,1-diamino-2,2-dinitroethylene (FOX-7) or an N-substituted diamino derivative thereof or a salt of 1,1-diamino-2,2-dinitroethylene or of the N-substituted diamino derivative is provided in accordance with the invention, where a carbodiimide is reacted with a dinitromethane anion. The reaction of the carbodiimide with the dinitromethane anion takes place in a solution. The reaction can be carried out in particular in a polar aprotic solvent, such as dimethylformamide (DMF) for example.

The carbodiimide can be in particular $C(NH)_2$, which is present with cyanamide in a tautomeric equilibrium. In the reaction, a nucleophilic addition to the carbodiimide takes place. The reaction is shown schematically in FIG. 1. In the reaction shown in FIG. 1, a salt of FOX-7 is formed. The salt can be converted into FOX-7 by acidification or neutralization of the or of a solution containing the salt. This synthesis is considerably more cost-effective to carry out than the syntheses known from the prior art. Moreover, the synthesis is considerably less hazardous, since no hazardous nitration step is required in this case and the reaction proceeds at a comparatively low temperature and in which also the use of the sensitive and explosive dinitromethane anion does not present a safety problem. Furthermore, the reaction proceeds in solution and the product can be precipitated and filtered off. The starting materials carbodiimide and dinitromethane are comparatively inexpensive.

A protic solvent can be added to the polar aprotic solvent. The protic solvent can be water or an alcohol, in particular an alkyl alcohol, particularly methanol, ethanol or propanol. The protic solvent in this case can supply hydrogen atoms favoring the course of the reaction and thereby increase the reaction rate. Since carbodiimide decomposes very readily by hydrolysis or alcoholysis, only a comparatively low amount of protic solvent should be added. The protic solvent should be added only at, or shortly after, the start of the reaction.

In one configuration of the method, the reaction takes place at a pH in the range of 6.5 to 7.5. A good yield is achieved in this case. The dinitromethane anion may be associated with a potassium ion or an ammonium ion as counterion.

A 1,1-diamino-2,2-dinitroethylene anion formed in the synthesis may be converted into 1,1-diamino-2,2-dinitroethylene (FOX-7) by lowering the pH of the/a solution comprising the 1,1-diamino-2,2-dinitroethylene anion. The solution can be the solution in which the synthesis has been carried out. It is also possible, however, to separate the 1,1-diamino-2,2-dinitroethylene anion in the form of a salt from the solution in which the synthesis has been carried out, and then said salt is dissolved in the same or another solvent to form the solution mentioned.

The invention is illustrated in more detail by means of a working example below.

Other features which are considered as characteristic for the invention are set forth in the appended claims.

Although the invention is illustrated and described herein as embodied in a method for synthesizing 1,1-diamino-2,2-dinitroethylene (fox-7) or a salt thereof, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
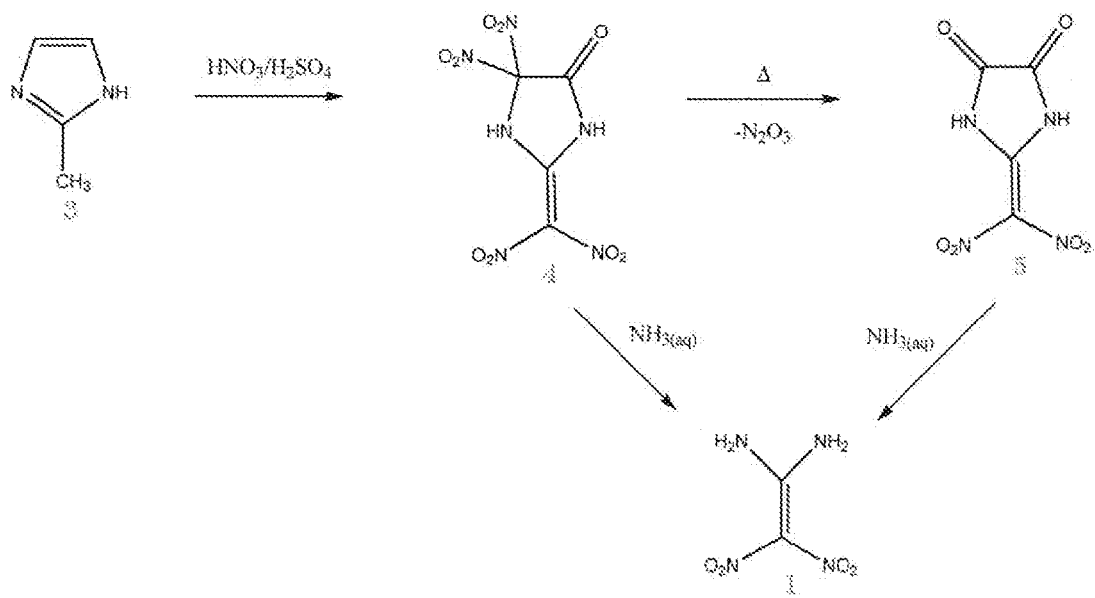
FIG. 1 shows a reaction scheme of a synthesis of FOX-7 from nitration of a nitrogen heterocycle with subsequent hydrolysis to an end product.
Figure 2:
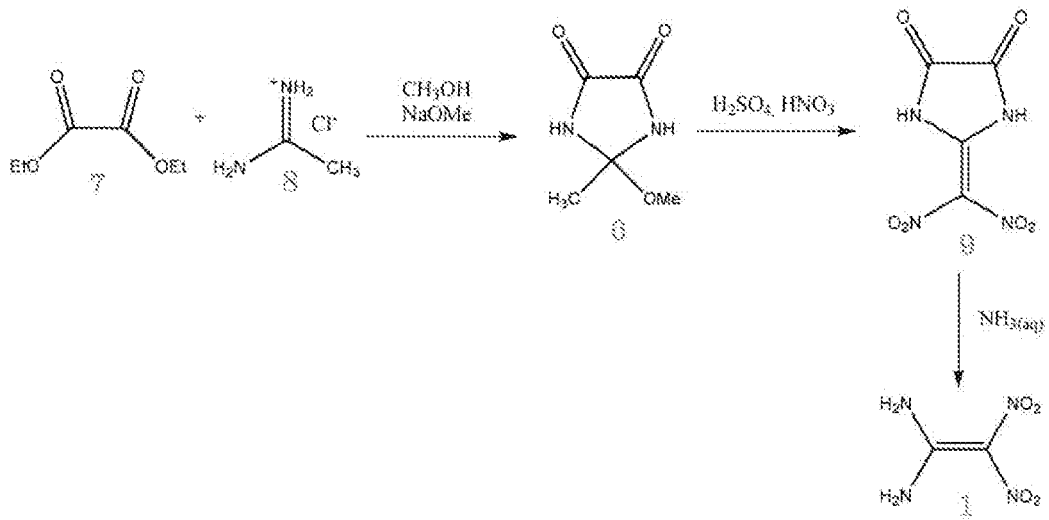
FIG. 2 shows a reaction scheme of a synthesis of FOX-7 from nitration of 2-methyl-2-methoxyimidazoledione.
Figure 3:
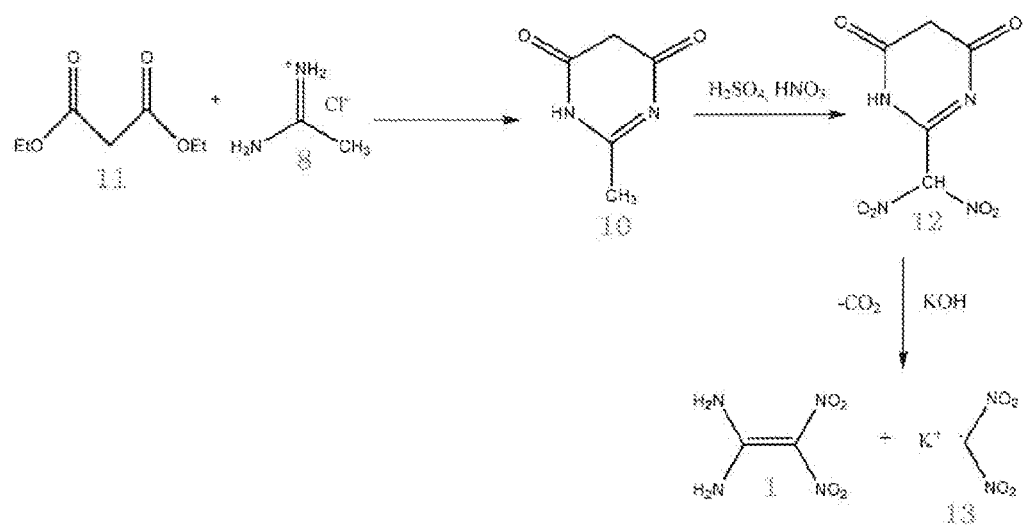
FIG. 3 shows a reaction scheme of a synthesis of FOX-7 from nitration of 2-methyl-4,6-pyrimidinedione.
Figure 4:
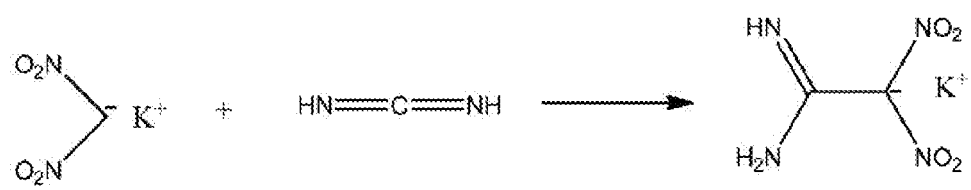
FIG. 4 shows a reaction scheme of the synthesis of KFOX-7 from carbodiimide.

To carry out the reaction shown in FIG. 4, 778 mg (5.4 mmol) of potassium dinitromethanate are dissolved in 20 ml of DMF at 60° C. in a 50 ml beaker and 226 mg (5.4 mmol) of carbodiimide in the form of $C(NH)_2$ are added. The solution is stirred at 60° C. for 2 hours and then allowed to cool to room temperature with stirring. After distilling off the solvent, the residue is dried in an explosion-proof drying oven at 50° C. and then measured thermoanalytically by dynamic differential scanning calorimetry (DSC) and also by IR, NMR and mass spectroscopy. The results are shown in Table 1 below.

TABLE 1

| Analysis | Reaction product | KFOX-7 reference |
|---|---|---|
| 1H-NMR (400 MHz) | 8.54 ppm (s) | 8.8 ppm (s) (FOX-7) |
| 13C-NMR (400 MHz) | 158.4 ppm (s) | 158.41 ppm (s) (KFOX-7) |
| Mass spectrum | 148.3 m/z | 148.1 m/z (FOX-7) |
| DSC | 230° C. | 228° C. (KFOX-7) |

Comparison with the KFOX-7 reference shows that the reaction product comprises the 1,1-diamino-2,2-dinitroethylene anion.

In the working example, it is also possible to use ammonium dinitromethanate in place of potassium dinitromethanate and/or also another carbodiimide in place of $C(NH)_2$.

The invention claimed is:

1. A method for synthesizing 1,1-diamino-2,2-dinitroethylene (FOX-7) or an N-substituted diamino derivative thereof or a salt of the 1,1-diamino-2,2-dinitroethylene or of the N-substituted diamino derivative, which comprises the step of:

reacting a carbodiimide with a dinitromethane anion.

2. The method according to claim 1, which further comprises forming the carbodiimide as $C(NH)_2$.

3. The method according to claim 1, which further comprises performing the reacting of the carbodiimide with the dinitromethane anion in a polar aprotic solvent.

4. The method according to claim 3, which further comprises providing dimethylformamide (DMF) as the polar aprotic solvent.

5. The method according to claim 3, which further comprises adding a protic solvent to the polar aprotic solvent.

6. The method according to claim 5, which further comprises selecting the protic solvent from the group consisting of water and alcohol.

7. The method according to claim 3, which further comprises performing the reacting step at a pH in a range of 6.5 to 7.5.

8. The method according to claim 3, wherein the dinitromethane anion is associated with a potassium ion or an ammonium ion as a counterion.

9. The method according to claim 1, which further comprises converting a 1,1-diamino-2,2-dinitroethylene anion formed in the synthesis into the 1,1-diamino-2,2-dinitroethylene by lowering a pH of a solution containing the 1,1-diamino-2,2-dinitroethylene anion.

* * * * *